United States Patent
Alexandre et al.

(10) Patent No.: US 7,455,655 B2
(45) Date of Patent: Nov. 25, 2008

(54) NEEDLELESS INJECTION DEVICE COMPRISING MEANS FOR REGULATING THE GAS PRESSURE LEVEL IN THE COMBUSTION CHAMBER

(75) Inventors: Patrick Alexandre, Gray (FR); Bernard Brouquieres, Toulon (FR); David Desailly, Vert le Petit (FR)

(73) Assignee: Crossject, Paris (FR)

( * ) Notice: Subject to any disclaimer, the term of this patent is extended or adjusted under 35 U.S.C. 154(b) by 169 days.

(21) Appl. No.: 10/547,997

(22) PCT Filed: Mar. 18, 2004

(86) PCT No.: PCT/FR2004/000659

§ 371 (c)(1),
(2), (4) Date: Sep. 12, 2005

(87) PCT Pub. No.: WO2004/084977

PCT Pub. Date: Oct. 7, 2004

(65) Prior Publication Data

US 2006/0089595 A1    Apr. 27, 2006

(30) Foreign Application Priority Data

Mar. 21, 2003   (FR) .................................. 03 03496

(51) Int. Cl.
*A61M 5/30*    (2006.01)
(52) U.S. Cl. ................................ 604/69; 604/68; 604/72

(58) Field of Classification Search ................... 604/68, 604/69, 71, 72, 140–148; 128/200.14–200.23
See application file for complete search history.

(56) References Cited

U.S. PATENT DOCUMENTS

| | | | | |
|---|---|---|---|---|
| 3,308,818 A | * | 3/1967 | Rutkowski | 604/69 |
| 3,802,430 A | * | 4/1974 | Schwebel et al. | 604/69 |
| 6,258,063 B1 | | 7/2001 | Haar et al. | |
| 6,328,714 B1 | * | 12/2001 | Bellhouse et al. | 604/232 |
| 7,160,265 B2 | * | 1/2007 | Lell | 604/69 |

FOREIGN PATENT DOCUMENTS

| | | |
|---|---|---|
| FR | 2 815 544 A1 | 4/2002 |
| WO | WO 00/44421 A1 | 8/2000 |
| WO | WO 01/97880 A2 | 12/2001 |

* cited by examiner

*Primary Examiner*—Kevin C. Sirmons
*Assistant Examiner*—Elizabeth R MacNeill
(74) *Attorney, Agent, or Firm*—Oliff & Berridge, PLC

(57) ABSTRACT

The invention relates to a needleless injection device (1) comprising a body (2) which supports and/or defines a plurality of elements that form a circuit of elements. The aforementioned circuit comprises, from upstream towards downstream, an initiation device which is associated with a pyrotechnic gas generator, a receptacle (5) housing a liquid active agent that is to be injected, and an active agent injection system. According to the invention, the pyrotechnic gas generator comprises a pyrotechnic charge (62) which is placed in a combustion chamber (4). The inventive device is characterised in that it comprises at least one device for regulating the gas pressure level in the combustion chamber (4).

10 Claims, 3 Drawing Sheets

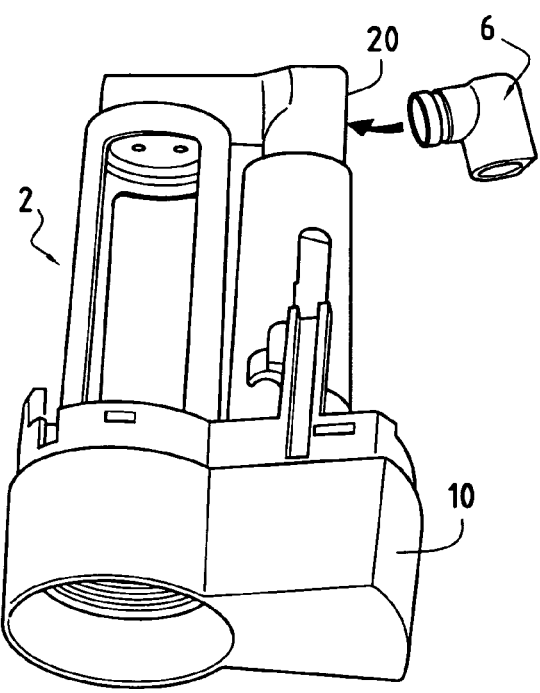
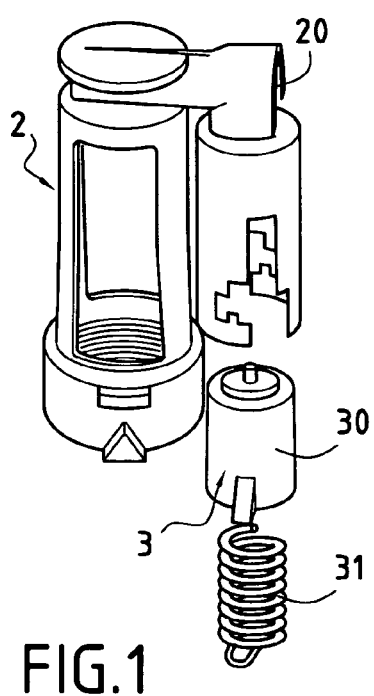
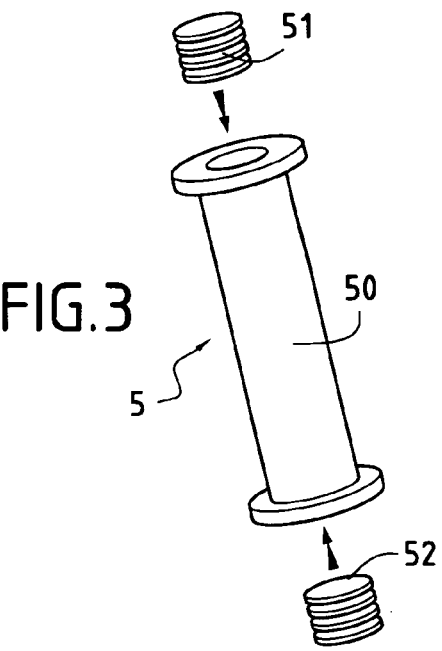
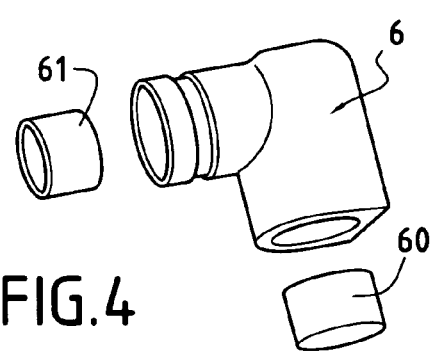
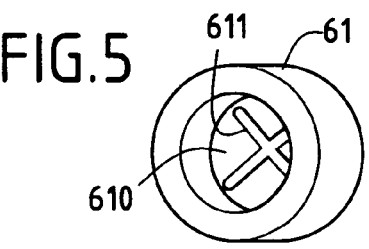

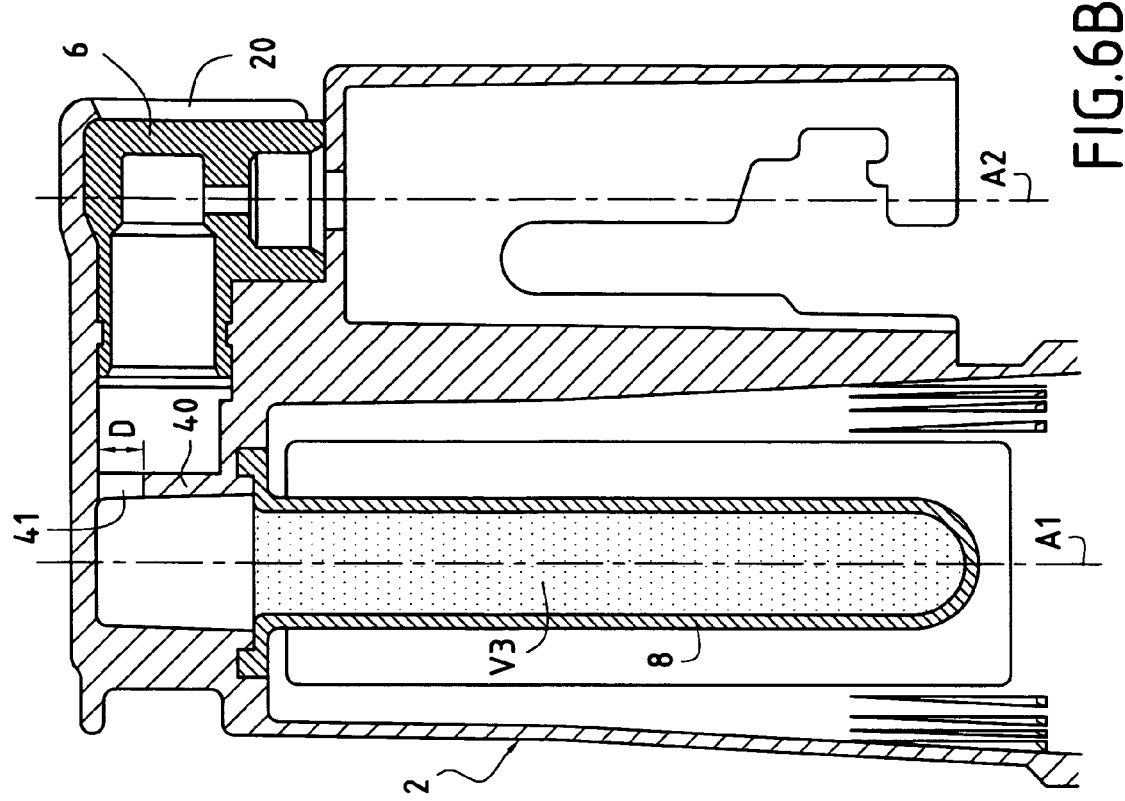
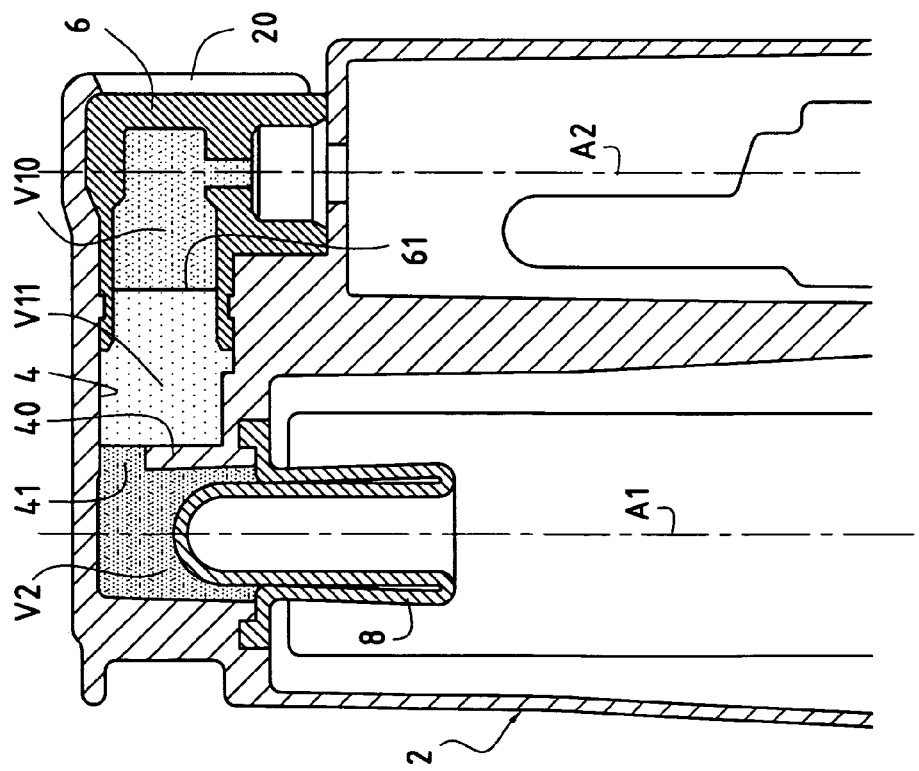

NEEDLELESS INJECTION DEVICE COMPRISING MEANS FOR REGULATING THE GAS PRESSURE LEVEL IN THE COMBUSTION CHAMBER

The technical field of the invention is that of pre-filled disposable needleless injection devices operating with a gas generator and used for intradermal, subcutaneous and intramuscular injections of liquid active principle for therapeutic use in human or veterinary medicine.

The active principle consists of a liquid of some viscosity, a mixture of liquids, or a gel. The active principle may equally be a solid dissolved in a solvent suitable for injection or consist of a pulverant solid in suspension at a certain concentration in a suitable liquid. The particle size of the active principle has then to be compatible with the diameter of the ducts so as to avoid blocking them.

When a needleless injection device uses, for injecting a liquid active principle, a pyrotechnic gas generator, the mechanical, thermal and dynamic stresses generated on the device by the gases originating from the combustion of the pyrotechnic charge of the generator are very high. The presence of these stresses therefore dictates that the device be strong enough to operate reliably and, in particular, not to disrupt the injection of active principle through the patient's skin.

The needleless injection device may be rendered strong and non-hazardous to its user by manufacturing it from materials which are themselves strong. However, these materials may prove to be expensive and heavy. Their use will therefore of necessity increase the cost of manufacture of the device and the mass of this device. Now, obviously the cost of manufacture of a disposable needleless injection device needs to remain as low as possible and such a device needs to remain easy to handle so that it can be used with facility by most people, especially the elderly.

The object of the invention is therefore to propose a disposable needleless injection device which is lightweight, easy to handle, has a low cost of manufacture and in which, also, the mechanical, thermal and dynamic stresses are limited.

This object is achieved by a disposable needleless injection device comprising a body supporting and/or delimiting a plurality of elements forming a circuit of elements, this circuit comprising, from upstream to downstream, an initiation device associated with a pyrotechnic gas generator, a reservoir containing a liquid active principle that is to be injected and a system for injecting the active principle, the pyrotechnic gas generator comprising a pyrotechnic charge placed in a combustion chamber, the device being characterized in that it comprises at least one device for regulating the pressure level of the gases in the combustion chamber. Thus, by using, in order to limit the stresses, a special device for regulating the pressure level in the combustion chamber, a needleless injection device is obtained which is reliable, able to withstand the stresses, and of low mass, which can therefore be handled by most people.

According to one particular feature, the device for regulating the pressure level of the gases is placed in the combustion chamber.

According to another particular feature, the combustion chamber is divided into two volumes by a wall, these two volumes being defined, from upstream to downstream, as a first and a second volume, the two volumes communicating via a first device for regulating the pressure level, the pyrotechnic charge being placed in the first volume.

According to another particular feature, the first device for regulating the pressure level consists of a passage formed through the wall. Thus, the flow rate of gases arriving in the reservoir to drive the active principle is controlled and mastered and this makes it possible to limit the thermal, dynamic and mechanical stresses on the reservoir as the device operates and thus avoid damage to the device and injury to its user.

According to another particular feature, the pyrotechnic charge is arranged in a first sub-volume of the first volume of the combustion chamber, this first sub-volume being initially closed.

According to another particular feature, the first sub-volume of the first volume of the combustion chamber is separated, by a second device for regulating the pressure level, from a second sub-volume of the first volume of the combustion chamber which is situated downstream of the first sub-volume. For example, if the combustion of the pyrotechnic charge is incomplete or poor, the active principle will not correctly penetrate through the skin and to the required depth. According to the invention, by using this second regulating device, the issue is therefore one of ensuring perfect combustion of the pyrotechnic charge and of keeping the pyrotechnic charge in a closed volume until almost all, and even ideally all, the pyrotechnic charge has burnt.

According to another particular feature, the second regulating device consists of a calibrated rupture disk. The rupture disk will open up, for example, into petals along a rupture initiator, the petals remaining secured to the rupture disk after opening. In this way, the projection of hot and aggressive particles into the combustion chamber is avoided.

According to another particular feature, the first sub-volume of the first volume, in which the pyrotechnic charge is placed, is delimited in part by the walls of a cartridge inserted in the body of the device. This first sub-volume is therefore formed independently of the body of the device. According to the invention, by using an independent gas-generating cartridge, it is possible, during the process of assembling the device, to tailor the quantity of pyrotechnic charge to the nature and/or quantity of active principle to be injected and to the desired depth of penetration of said active principle.

According to another particular feature, the pyrotechnic charge is placed in the cartridge between the calibrated rupture disk and a detonator able to initiate the pyrotechnic charge.

According to another particular feature, the cartridge has the shape of an L-shaped duct in which the pyrotechnic charge is placed, this duct being blocked off at one of its ends by the detonator and at its other end by the calibrator rupture disk. This shape is particularly suited to a needleless injection device of compact form.

According to another particular feature, the combustion chamber comprises a third volume, situated downstream of the second volume, this third volume being created as the device operates.

According to one particular feature, the third volume is delimited by an expanding membrane deployed under the action of the gases originating from the combustion of the pyrotechnic charge.

According to another particular feature, the membrane deploys into the reservoir of active principle.

According to another particular feature, the membrane constitutes a sealed wall between the combustion chamber and the reservoir of active principle. According to the invention, given the need to keep the active principle clean as the device operates, this membrane is interposed between the combustion chamber and the reservoir to prevent the combustion gases from contaminating the active principle. The membrane must be made of a material that is flexible enough and strong enough to be able to deploy under the action of the gases and drive the active principle contained in the reservoir.

According to another particular feature, the passage is offset from a longitudinal central axis of the combustion chamber and is formed in such a way as to be as far as possible away from the membrane. In order to prevent the hot and aggressive gases leaving the first volume from coming into contact directly with the initially-folded membrane and damaging it, the passage is offset from the axis of the combustion chamber.

According to another particular feature, the circuit of elements forms an inverted U-shape therefore comprising two parallel branches connected to one another by a transverse branch. This type of architecture gives the device a compact, ergonic and low-bulk shape.

The invention, with its characteristics and advantages, will become more clearly apparent from reading the description given with reference to the attached drawings in which:

FIG. 1 depicts, in perspective and in an exploded view, the body of the device together with some of the elements intended to be assembled on the body of the device.

FIG. 2 depicts, in perspective, the body of the device onto which certain elements have been assembled, together with the gas-generating cartridge.

FIG. 3 depicts, in perspective and in an exploded view, the reservoir intended to accommodate the liquid active principle.

FIG. 4 depicts, in perspective and in an exploded view, a pyrotechnic gas-generating cartridge used in the device according to the invention.

FIG. 5 depicts, in perspective, a rupture disk as used in the pyrotechnic cartridge of FIG. 4.

FIGS. 6A and 6B depict, in longitudinal section, the body of the device before operation and after operation respectively. These FIGS. 6A and 6B more particularly depict the various volumes of the combustion chamber of the device.

Figure 7:
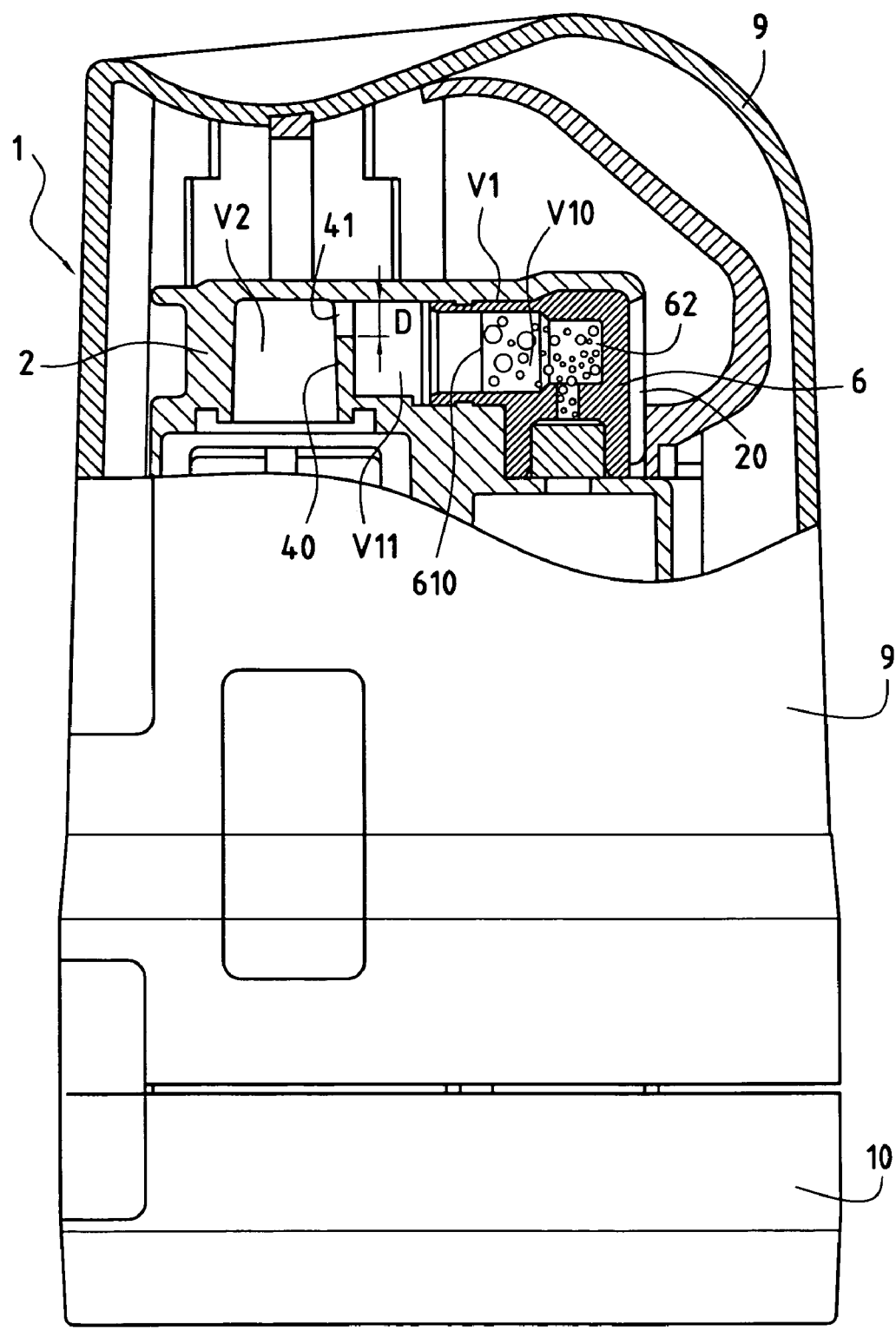
FIG. 7 depicts, in longitudinal part section, a needleless injection-device according to the invention, not actuated, in which the pyrotechnic cartridge depicted in FIG. 4 is inserted.

A needleless injection device 1 according to the invention, depicted in FIG. 7, comprises a hollow body 2 in the shape of an inverted U inserted under a cap 9 for actuating the device 1, this cap being blocked off by a stopper 10. This U-shape gives the device a compact form the advantages of which are more particularly described in patent No. FR 2 815 544. Actuation of such a device 1 by the patient, using the cap 9, is also described in patent FR 2 815 544. During the process of assembling the device 1, this body 2 is intended to accommodate a plurality of elements. Thus, once assembled, the body 2, depicted in FIG. 1, comprises or delimits successively, from upstream to downstream, a percussion device 3 comprising a striker 30 and a spring 31, a detonator 60, a pyrotechnic charge 62 (FIG. 7), these three elements forming a gas generator, a combustion chamber 4, a reservoir 5 (FIG. 3) containing a liquid active principle to be injected, and an injection system (not visible). The gas generator constitutes a first linear subassembly inserted in the body 2 along a first vertical branch of the inverted U formed by the body 2. The reservoir 5 containing the active principle to be injected and the injection system form a second linear subassembly inserted along the second vertical branch of the inverted U formed by the body 2. The first and second subassemblies are linear along two axes (A1, A2, FIGS. 6A and 6B) which are parallel and are connected to one another by the combustion chamber 4 which is formed in the body 2 along an axis perpendicular to the axes (A1, A2) of the two subassemblies, that is to say along the transverse branch connecting the two parallel branches of the inverted U formed by the body 2.

The reservoir 5 depicted in FIG. 3 consists, for example, of a glass tube 50 open at both ends. The tube 50 is inserted in the body 2 in such a way as to be connected, at its most upstream end, to the combustion chamber 4, and at its most downstream end, to the injection system. The active principle (not depicted) is, for example, trapped in the glass tube 50 between an upstream stopper-piston 51 and a downstream stopper-piston 52 pushed into the tube 50. The upstream 51 and downstream 52 stopper-pistons are made for example of an elastomer-based deformable material.

The injection system in particular comprises an injection nozzle through which the active principle contained in the reservoir 5 is injected. This injection nozzle comprises, for example, a plurality of injection channels along which the liquid is intended to pass at the time of injection.

According to the invention, the combustion chamber 4 is split into a plurality of successive adjacent volumes V1, V2 each having a clearly determined function. These volumes are formed along the axis defined by the transverse branch of the inverted U formed by the body 2.

A transverse wall 40 situated in the combustion chamber 4 splits the combustion chamber 4 into two distinct volumes V1, V2 formed in the body. A nozzle 41 or passage, of a determined diameter D (FIGS. 6B and 7) is formed on the wall 40 to cause the two volumes V1, V2 to communicate. The first volume V1 defined as the volume situated furthest upstream is itself split into two sub-volumes V10, V11. Placed in a first sub-volume V10 situated furthest upstream is the gas-generating pyrotechnic charge 62. More specifically, this first sub-volume V10 is defined in a gas-generating cartridge 6 in which the pyrotechnic charge 62 is placed. The cartridge 6 is inserted into a specific housing provided for it in the combustion chamber 4. This housing follows the right angle defined between the combustion chamber 4 for the gases and the first vertical branch of the U formed by the body 2. An opening 20 communicating with the housing is formed on the body 2. This opening 20 is formed laterally on the body 2, more or less along the axis of the combustion chamber 4 for the gases.

According to the invention, the gas generator therefore comprises a gas-generating cartridge 6 inserted in the body 2 of the device 1 via a specific opening 20 formed on the body 2. The cartridge 6 is then crimped onto the body 2 at the opening 20. The gas-generating cartridge 6 depicted in FIGS. 2 and 4 is, for example, made of metal and comprises a detonator 60 and a pyrotechnic charge 62 (FIG. 7) enabling the quantity of gas needed to cause the injection of the active principle to be generated. The detonator 60 is, for example, of the kind used in a cartridge for a hunting gun. The pyrotechnic charge 62 consists of a powder able to emit a large quantity of gas such as, for example, a simple nitrogen cellulose-based powder. With reference to FIG. 4, the gas-generating cartridge 6 used in the needleless injection device 1 according to the invention is, for example, in the shape of an L-shaped duct in which the pyrotechnic charge 62 is placed. When the cartridge 6 is set into the device 1 as depicted in FIG. 7, the L-shape follows the right angle formed between the first vertical branch of the inverted U formed by the body 2 and its transverse branch. Furthermore, once the cartridge 6 is in place in the housing, the most upstream end of the duct forming the cartridge 6 is blocked off by the detonator 60 while the most downstream end of the duct is blocked off by a calibrated rupture disk 61. The rupture disk 61 blocking off the L-shaped duct formed by the cartridge 6 at its downstream end therefore lies along the axis of the combustion chamber 4 and the detonator 60 blocking off said duct at its upstream end lies along the axis of the first subassembly and, more particularly, along the axis of the striker 30.

The rupture disk 61, depicted in greater detail in FIG. 5, constitutes a device for regulating the pressure level in the combustion chamber 4 and is in the form of a cylindrical stopper pushed into the canal of the duct formed by the cartridge 6. This stopper comprises a wall 610 perpendicular to the axis of the duct, blocking off the duct, and on which a rupture initiator 611 is formed. The rupture initiator 611 constitutes an area of weakness along which, under a certain gas pressure, the disk 61 yields and opens up into petals. Once the disk has opened up, the petals remain secured to the disk 61 and this prevents them from being projected into the remainder of the device 1. The rupture or opening threshold for the rupture disk 61 is determined by the depth of the rupture initiator 611 formed on the wall 610. The pyrotechnic charge 62 is placed in the duct formed by the cartridge 6 between the detonator 60 and the rupture disk 61. The pyrotechnic charge 62, before the disk 61 yields, is therefore completely isolated from the remainder of the combustion chamber 4. The disk 61 will yield, for example, once almost all of the pyrotechnic charge 62 has burnt. By thus regulating the rupture threshold of the disk 61, the pyrotechnic charge 62 is kept in a closed and small volume during its combustion, and this prevents some of the grains of powder from being projected into the remainder of the combustion chamber 4 and thus remaining unburnt. This then makes it possible to obtain optimum yield and give the device 1 great reliability. The second sub-volume v11 of the first volume V1 of the combustion chamber, defined in the first volume V1 by the space not occupied by the cartridge 6 and situated downstream of the first sub-volume V10, that is to say on the outlet side of the calibrated rupture disk 61, communicates with the second volume V2 of the combustion chamber via the nozzle 41. The nozzle 41 thus constitutes a second device for regulating the pressure level of the gases in the combustion chamber 4 and allows the velocity of the gases leaving the cartridge 6 to be reduced. According to the invention, the slowing of the gases makes it possible in particular to reduce the mechanical shock generated, at the time of injection, by the downstream stopper-piston 52 against the injection system.

The U-shape of the device 1 and, more particularly, the misalignment between the combustion chamber 4 and the reservoir 5 of liquid active principle also makes it possible to break the shockwave generated at the start of the combustion of the pyrotechnic charge 62.

According to the invention, the combustion chamber 4 comprises a third volume V3 situated downstream of the second volume V2. This volume V3 is created, at the time of operation of the device 1, in the reservoir 5 by the combustion gases. This volume V3 is formed more precisely in the glass tube 50 between the second volume V2 and the upstream stopper-piston 51. This third volume V3 therefore increases with the movement of the upstream stopper-piston 51, this movement being created as the device 1 operates by the combustion gases. This third volume V3 is more particularly delimited by a membrane 8, initially filled as depicted in FIG. 6A, deploying into the reservoir 5 under the action of the gases and, under the effect of said gases, driving the upstream stopper-piston 51. This membrane 8 has the shape of a cap made of an extensile material, resistant to heat and to ageing, such as rubber for example. According to the invention, the presence of this membrane 8 is not compulsory but it does make it possible to limit the risk of the active principle contained in the reservoir 5 becoming contaminated by the combustion gases. It therefore constitutes a sealed wall between the combustion gases and the liquid active principle. According to the invention, the nozzle 41 is produced through the wall 40 so as to be as far away as possible from the membrane 8 so that the hot gases passing through it do not come too much into contact with the membrane and thus do not damage it. As depicted in FIGS. 6A, 6B and 7, the nozzle 41 is formed along an axis situated, when the device is placed on its stopper, in a parallel horizontal plane higher than the one containing the axis of the combustion chamber 4.

The way in which such a needleless injection device 1 having components such as those defined in this application works is described in detail in French patent application FR 2 815 544. The overall operation of such a device 1 may, however, be summarized as follows:

at rest, the striker 30 rests, for example, against a stop with the aid of a preloaded spring 31 the axis of which is more or less coincident with the axis of the striker 30. A particular manipulation on the part of the user releases the striker 30 which, under the effect of the relaxation of the spring 31, will strike the detonator 60 situated along the same axis. Initiation of the detonator 60 then leads to ignition of the pyrotechnic charge 62 contained in the cartridge 6. When a certain gas pressure is reached in the cartridge 6 and when the rupture threshold of the rupture disk 61 is reached, the rupture disk 61 opens up along its rupture initiator 611 and thus allows the gases to pass into the second sub-volume V11 of the first volume V1 of the combustion chamber 4. The gases present in the second sub-volume V11 are then slowed as they pass through the nozzle 41 formed on the wall 40 separating the first volume V1 from the second volume V2 of the combustion chamber 4. Regulating the diameter of the nozzle makes it possible to master the pressurizing of the second volume V2 and thus, as a result, to limit the stresses on the membrane 8. The gases present in the second volume V2 enter the third volume V3 formed at right angles. Under the action of the gases, the membrane 8 unfolds and, as it expands, pushes against the upstream stopper-piston 51 present in the tube 50 of the reservoir 5. The upstream stopper-piston 51 in turn drives the active principle towards the injection system and the active principle is thus ejected from the device 1.

In FIG. 6B, the body 2 depicted is that of a device which has already operated, that is to say in which the membrane 8 has been deployed and the cartridge 6, following combustion of all of the pyrotechnic charge 62, has been emptied.

According to the invention, the first sub-volume V10 will, for example, have a volume of 99 mm$^3$, the second sub-volume V11 a volume of 149 mm$^3$, the second volume V2 a volume of 153 mm$^3$ and the third volume V3, 599 mm$^3$. In such a configuration, the nozzle will, for example, have a diameter of 2 mm.

According to the invention, successive mastering of the pressure level in each of the volumes V1, V2, V3 right up to deployment of the membrane 8 makes it possible to control the mechanical, dynamic and thermal stresses on the components that delimit the combustion chamber 4. According to the invention, the objectives of cost, mass and ergonomics of the device can therefore be met. In addition, successive mastering of the pressure level in the various volumes V1, V2, V3 also allows the mechanical and dynamic behavior of the elements situated downstream of the combustion chamber 4 and on which the skin penetration performance depends to be controlled.

It must be obvious to those skilled in the art that the present invention allows embodiments in numerous other specific forms without departing from the field of application of the invention as claimed. In consequence, the present embodiments are to be considered by way of illustration, but may be modified within the field defined by the scope of the attached claims, and the invention must not be limited to the details given hereinabove.

The invention claimed is:

1. A disposable needleless injection device comprising a body supporting or delimiting a plurality of elements forming a circuit of elements, the circuit comprising, from upstream to downstream, an initiation device associated with a pyrotechnic gas generator, a reservoir containing a liquid active principle that is to be injected and a system for injecting the active principle, the pyrotechnic gas generator comprising a pyrotechnic charge placed in a combustion chamber, said combustion chamber being divided into two volumes by a wall, the two volumes being defined, from upstream to downstream, as a first volume in which the pyrotechnic charge is placed and a second volume, the two volumes communicating via a first device for regulating a pressure level in the combustion chamber, the injection device further comprising a membrane, furled before operation, constituting a sealed wall between the combustion chamber and the reservoir of active principle, said membrane being able, in operation, to deploy under the action of the gases originating from the combustion of the pyrotechnic charge, wherein the membrane is a cylindrical tube having a closed end and an open end, the closed end being positioned, before operation of the device, in the second volume of the combustion chamber and being positioned, after operation of the device, within the reservoir of active principle, and the membrane includes a flange extending radially outward at the open end, the closed end being positioned, before the operation of the device, upstream of the flange.

2. The device as claimed in claim 1, wherein the first device for regulating the pressure level includes a passage formed through the wall.

3. The device as claimed in claim 1, wherein the pyrotechnic charge is arranged in a first sub-volume of the first volume of the combustion chamber, this first sub-volume being initially closed.

4. The device as claimed in claim 3, wherein the first sub-volume of the first volume of the combustion chamber is separated, by a second device for regulating the pressure level, from a second sub-volume of the first volume of the combustion chamber which is situated downstream of the first sub-volume.

5. The device as claimed in claim 4, wherein the second regulating device includes a calibrated rupture disk.

6. The device as claimed in claim 5, wherein the first sub-volume of the first volume, in which the pyrotechnic charge is placed, is delimited in part by the walls of a cartridge inserted in the body of the device.

7. The device as claimed in claim 6, wherein the pyrotechnic charge is placed in the cartridge between the calibrated rupture disk and a detonator able to initiate the pyrotechnic charge.

8. The device as claimed in claim 7, wherein the cartridge has the shape of an L-shaped duct in which the pyrotechnic charge is placed, the duct being blocked off at one of its ends by the detonator and at its other end by the calibrator rupture disk.

9. The device as claimed in claim 2, wherein the membrane deploys into the reservoir of active principle.

10. The device as claimed in claim 9, wherein the passage is offset from a longitudinal central axis of the combustion chamber and is formed in such a way as to be as far as possible away from the membrane.

* * * * *